United States Patent [19]
Pevarello et al.

[11] Patent Number: 5,945,454
[45] Date of Patent: Aug. 31, 1999

[54] 2-(4-SUBSTITUTED)-BENZYLAMINO-2-METHYL-PROPANAMIDE DERIVATIVES

[75] Inventors: Paolo Pevarello, Pavia; Raffaella Amici, Piacenza; Mario Varasi, Milan; Alberto Bonsignori, Milan; Patricia Salvati, Milan, all of Italy

[73] Assignee: Pharmacia & Upjohn, S.P.A., Milan, Italy

[21] Appl. No.: 08/981,492

[22] PCT Filed: Jul. 5, 1996

[86] PCT No.: PCT/EP96/02961

§ 371 Date: Jan. 8, 1998

§ 102(e) Date: Jan. 8, 1998

[87] PCT Pub. No.: WO97/05102

PCT Pub. Date: Feb. 13, 1997

[30] Foreign Application Priority Data

Jul. 27, 1995 [GB] United Kingdom .................. 9515412

[51] Int. Cl.⁶ ....................... A61K 31/165; C07C 233/05
[52] U.S. Cl. .................. 514/620; 514/618; 514/619; 564/162; 564/163; 564/164; 564/167; 564/171
[58] Field of Search ...................... 564/162, 163, 564/164, 167, 171; 514/618, 620, 619

[56] References Cited

FOREIGN PATENT DOCUMENTS

| | | |
|---|---|---|
| 9014334 | 11/1990 | WIPO. |
| 9422808 | 10/1994 | WIPO. |
| 9422809 | 10/1994 | WIPO. |

OTHER PUBLICATIONS

Euerby et al, Jouranal Chemical Research(M), No. 9, abstract 2419–2427, 1982.

*Primary Examiner*—Shailendra Kumar
*Attorney, Agent, or Firm*—Nikaido Marmelstein Murray & Oram, LLP

[57] ABSTRACT

Novel 2(4-substituted)-benzylamino-2-methyl-propanamides compounds, having CNS activity, of general formula (I) wherein: n is zero, 1, 2 or 3; X is —O—, —S—, —CH$_2$— or —NH—; each of R and R$_1$ independently is hydrogen, C$_1$–C$_6$ alkyl, halogen, hydroxy, C$_1$–C$_4$ alkoxy or trifluoromethyl; each of R$_2$, R$_3$ and R$_4$ independently is hydrogen, C$_1$–C$_6$ alkyl or C$_3$–C$_7$ cycloalkyl; and the pharmacetically acceptable salts thereof, are disclosed.

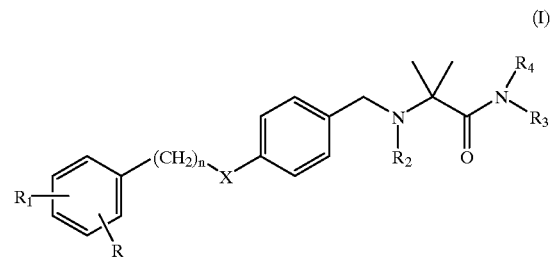

12 Claims, No Drawings

2-(4-SUBSTITUTED)-BENZYLAMINO-2-METHYL-PROPANAMIDE DERIVATIVES

This application is 371 of PCT/EP96/02961 filed Jul. 5, 1996.

The present invention relates to novel 2-(4-substituted)-benzylamino-2-methyl-propanamides, to their use as therapeutic agents, to a process for their preparation and to pharmaceutically compositions containing them.

WO 90/14334 discloses N-phenylalkyl substituted α-amino carboxamide derivatives active on the CNS.

It has been found that novel 2-(4-substituted)-benzylamino-2-methyl-propanamides derivatives as herein defined have valuable biological properties, in particular as antiepileptic, anti-Parkinson, neuroprotective, anti-depressant, antispastic and/or hypnotic agent.

The present invention provides novel compounds of the following general formula (I)

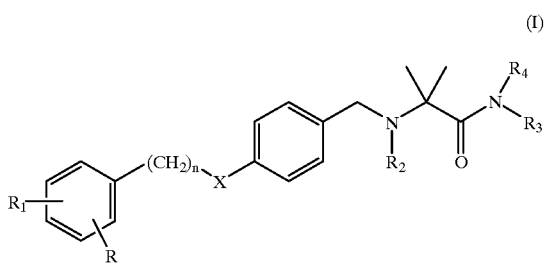

(I)

wherein:
n is zero, 1, 2 or 3;
X is —O—, —S—, —CH$_2$— or —NH—;
each of R and R$_1$ independently is hydrogen, C$_1$–C$_6$ alkyl, halogen, hydroxy, C$_1$–C$_4$ alkoxy or trifluoromethyl;
each of R$_2$, R$_3$ and R$_4$ independently is hydrogen, C$_1$–C$_6$ alkyl or C$_3$–C$_7$ cycloalkyl;
and the pharmaceutically acceptable salts thereof.

The pharmaceutically acceptable salts of the compounds of formula (I) include acid addition salts with inorganic, e.g. hydrochloric, hydrobromic, sulfuric, and phosphoric acids, or organic, e.g. acetic, propionic, lactic, oxalic, malic, maleic, tartaric, citric, benzoic, mandelic, C$_1$–C$_4$ alkylsulfonic, salicylic and fumaric acids.

The compounds of the formula (I), their pharmaceutically acceptable salts may also form pharmaceutically acceptable solvates, such as mono-, di- or tri-hydrates, which are also object of the present invention.

The alkyl and alkoxy groups may be branched or straight groups.

A C$_1$–C$_6$ alkyl group is preferably a C$_1$–C$_4$ alkyl group, in particular methyl, ethyl, n- and iso-propyl, n-, iso-, sec-and tert-butyl, more preferably methyl or ethyl. Representative examples of C$_1$–C$_4$ alkoxy groups include methoxy or ethoxy.

A halogen atom is e.g. chlorine, fluorine or bromine.

A C$_3$–C$_7$ cycloalkyl group is, for instance, a cyclopropyl, cyclohexyl or cycloheptyl group, in particular cyclopropyl. The present invention also include within its scope all the possible isomers of the compounds of formula (I) and their mixtures, as well as the metabolites and the pharmaceutically acceptable bio-precursors (otherwise known as pro-drugs) of the compounds of formula (I).

Preferred compounds of the invention are the compounds of formula (I) wherein
n is 1 or 2;
X is —O—, —S— or —NH—;
R is hydrogen;
R$_1$ is hydrogen or halogen;
each of R$_2$, R$_3$ and R$_4$ independently is hydrogen or C$_1$–C$_4$ alkyl; and the pharmaceutically acceptable salts thereof.

More preferred compounds of the invention are the compounds of formula (I), wherein
n is 1;
X is —O—, —S— or —NH—;
R$_1$ is hydrogen or halogen;
R, R$_2$, R$_3$ and R$_4$ are hydrogen; and the pharmaceutically acceptable salts thereof.

Examples of specific compounds of the invention are:

2-[4-(3-fluorobenzyloxy)benzylamino]-2-methyl-propanamide;

2-[4-(3-chlorobenzyloxy)benzylamino]-2-methyl-propanamide;

2-[4-(4-chlorobenzyloxy)benzylamino]-2-methyl-propanamide;

2-[4-(3-bromobenzyloxy)benzylamino]-2-methyl-propanamide;

2-[4-(4-fluorobenzyloxy)benzylamino]-2-methyl-propanamide;

2-[4-(2-fluorobenzyloxy)benzylamino]-2-methyl-propanamide;

2-[4-(3-fluorobenzylamino)benzylamino]-2-methyl-propanamide;

2-[4-(benzylsulfanyl)benzylamino]-2-methyl-propanamide;

2-[4-(3-fluorobenzyloxy)benzylmethylamino]-2-methyl-propanamide;

2-{[4-(3-fluorobenzyloxy)benzyl]-amino}-2-methyl-N-methyl-propanamide;

2-{[4-(3-chlorobenzyloxy)benzyl]methylamino}-2-methyl-propanamide; and

2-{[4-(3-bromobenzyloxy)benzyl]methylamino}-2-methyl-propanamide, if the case, either as single (S) or (R) isomer or as a mixture thereof, and the pharmaceutically acceptable salts thereof.

The compounds of the invention and the salts thereof can be obtained by a process comprising:

a) reacting a compound of formula (II)

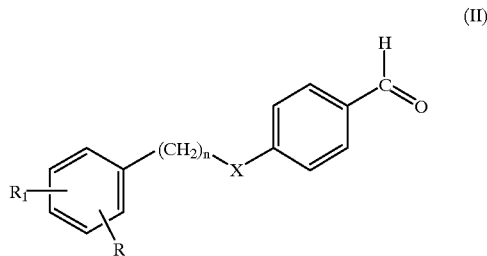

(II)

wherein n, R, R$_1$ and X are as defined above, with a compound of formula (III)

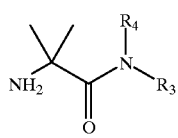
(III)

wherein $R_3$ and $R_4$ are as defined above, thus obtaining a compound of formula (I) in which $R_2$ is hydrogen; or b) reacting a compound of formula (IV)

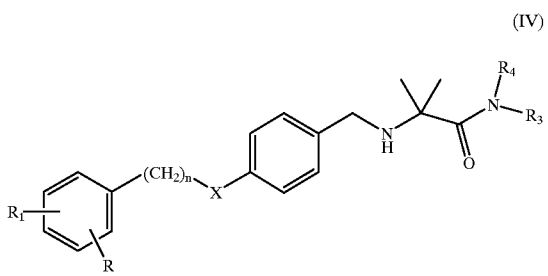
(IV)

wherein R, $R_1$, $R_3$, $R_4$, n and X are as defined above, with a compound of formula (V) or (VI)

(V)

(VI)

wherein W is a halogen atom; $R'_2$ is a $C_1$–$C_6$ alkyl and $R''_2$ is hydrogen or $C_1$–$C_5$ alkyl, thus obtaining a compound of the invention in which $R_2$ is $C_1$–$C_6$ alkyl; and, if desired, converting a compound of the invention into another compound of the invention and/or, if desired, converting a compound of the invention into a pharmaceutically acceptable salt and/or, if desired, converting a salt into a free compound.

All the processes described hereabove are analogy processes and can be carried out according to well known methods in organic chemistry.

A compound of formula (IV) is a compound of formula (I) in which $R_2$ is hydrogen.

The reaction of a compound of formula (II) with a compound of formula (III) to give a compound of formula (I) or (IV) is a reductive amination reaction which can be carried out according to well known methods. According to a preferred embodiment of the invention it may be performed under nitrogen atmosphere, in a suitable organic solvent, such as an alcohol, e.g. a lower alkanol, in particular methanol, or in acetonitrile, at a temperature ranging from about 0° C. to about 40° C., in the presence of a reducing agent, the most appropriate being sodium cyanoborohydride. Occasionally molecular sieves can be added to the reaction mixture for facilitating the reaction.

In a compound of formula (V) the halogen W is preferably iodine. The alkylation reaction of a compound of formula (IV) with a compound of formula (V) can be carried out in a suitable organic solvent, such as an alcohol, e.g. methanol, ethanol or isopropanol, in particular in ethanol, at a temperature ranging from about 0° C. to about 50° C.

The alkylation reaction of a compound of formula (IV) with an aldehyde of formula (VI) can be carried out in a suitable organic solvent, such as an alcohol, e.g. methanol, ethanol or acetonitrile in the presence of a suitable reducing agent, such as sodium cyanoborohydride, at a temperature ranging from about 0° C. to about 30° C.

A compound of the invention can be converted, as stated above, into another compound of the invention by known methods. Process-variant b) above may be regarded as an example of optional conversion of a compound of the invention into another compound of the invention.

Also the optional salification of a compound of the invention as well as the conversion of a salt into the free compound may be carried out by conventional methods.

The compounds of formula (II), (III), (V) and (VI) are known compounds or can be obtained by known methods. When in the compounds of the present invention and in the intermediate-products thereof, groups are present, which need to be protected before submitting them to the hereabove illustrated reactions, they may be protected before being reacted and then deprotected according to methods well known in organic chemistry.

PHARMACOLOGY

The compounds of the invention are active on the central nervous system (CNS) and can be used in therapy, for example as antiepileptics, in the treatment of Parkinson's disease and as neuroprotective agents, e.g. preventing or treating neuronal loss associated with stroke, hypoxia, ischemia, CNS trauma, hypoglycaemia or surgery and in treating and preventing neurodegenerative diseases such as Alzheimer's disease, amyotrophic lateral sclerosis, Down's syndrome, Huntington's disease, dementia caused by acquired immunodeficiency syndrome (AIDS), infarctual dementia and infections or inflammations in the brain; they can also be used as antidepressants, hypnotics and antispastic agents and in treating ocular damage and rethinopaty.

The activity on the CNS of the compounds of the invention was evaluated on the basis of pharmacological methods, such as, for example, the antagonism of convulsions and lethality induced by intravenous injection of bicuculline in mice (Antiepileptic Drugs, D. M. Woodbury et al. eds., 2nd edition, Raven Press, New York, 1982), or the antagonism of maximal electroshock seizures (MES) (Woodbury, L. A. and Davenport, V. D., Arch. Int. Pharmacodyn. Ther. 92; 97–104, 1952).

The following table summarizes the activity data obtained by testing in the MES test a representative group of compounds of the invention in comparison with the respective 2-desmethyl related compounds known from WO 90/14334.

The symbol * identifies the prior art 2-desmethyl-compounds known from WO 90/14334.

$ED_{50}$ means effective dose in 50% of treated animals after per os (po) administration.

TABLE 1

| Structure | Compound (internal code) | MES-ED$_{50}$ (po) mg/Kg |
|---|---|---|
| 3-F-C$_6$H$_4$-CH$_2$-O-C$_6$H$_4$-CH$_2$-NH-CH(CH$_3$)-C(O)NH$_2$ · CH$_3$SO$_3$H | FCE 26743A* | 8.2 (7.2–9.4) |
| 3-F-C$_6$H$_4$-CH$_2$-O-C$_6$H$_4$-CH$_2$-NH-C(CH$_3$)$_2$-C(O)NH$_2$ · CH$_3$SO$_3$H | FCE 29088A | 4.4 (2.8–6.3) |
| C$_6$H$_5$-CH$_2$-S-C$_6$H$_4$-CH$_2$-NH-CH(CH$_3$)-C(O)NH$_2$ · CH$_3$SO$_3$H | FCE 26727A* | 12.72 (9.19–17.62) |
| C$_6$H$_5$-CH$_2$-S-C$_6$H$_4$-CH$_2$-NH-C(CH$_3$)$_2$-C(O)NH$_2$ · CH$_3$SO$_3$H | FCE 29482A | 3.12 (2.28–4.27) |
| 2-F-C$_6$H$_4$-CH$_2$-O-C$_6$H$_4$-CH$_2$-NH-CH(CH$_3$)-C(O)NH$_2$ · CH$_3$SO$_3$H | FCE 26742A* | 7.13 (5.70–8.91) |
| 2-F-C$_6$H$_4$-CH$_2$-O-C$_6$H$_4$-CH$_2$-NH-C(CH$_3$)$_2$-C(O)NH$_2$ · CH$_3$SO$_3$H | FCE 29484A | 3.10 (2.25–4.28) |
| 3-Cl-C$_6$H$_4$-CH$_2$-O-C$_6$H$_4$-CH$_2$-NH-CH(CH$_3$)-C(O)NH$_2$ · CH$_3$SO$_3$H | FCE 26193A* | 9.41 (7.12–12.4) |

TABLE 1-continued

| Structure | Compound (internal code) | MES-ED$_{50}$ (po) mg/Kg |
|---|---|---|
| [structure: 3-chlorobenzyloxy-benzylamino-2-methyl-propanamide, methanesulfonate] | FCE 29644A | 3.88 (2.90–5.19) |
| [structure: (S)-4-fluorobenzyloxy-benzylamino propanamide, methanesulfonate] | FCE 26998A* | 16.30 (7.18–37.12) |
| [structure: 4-fluorobenzyloxy-benzylamino-2-methyl-propanamide, methanesulfonate] | FCE 29645A | 6.58 (4.02–16.97) |
| [structure: (S)-3-fluorobenzyloxy-benzylamino-N-methylpropanamide, methanesulfonate] | FCE 28657A* | 9.35 (4.34–13.11) |
| [structure: 3-fluorobenzyloxy-benzylamino-2-methyl-N-methylpropanamide, methanesulfonate] | FCE 29647A | 4.34 (3.28–5.75) | where internal code:
FCE 29088A means 2-(4-(3-fluorobenzyloxy) benzylamino)-2-methyl-propanamide, methanesulfonate;
FCE 26743A* means (S)-2-(4-(3-fluorobenzyloxy) benzylamino) propanamide, methanesulfonate;
FCE 29482A means 2-(4-benzylsulfanyl)benzylamino)-2-methyl-propanamide, methanesulfonate;
FCE 26727A* means (S)-2-(4-benzylsulfanyl)benzylamino) propanamide, methanesulfonate;
FCE 29484A means 2-(4-(2-fluorobenzyloxy) benzylamino)-2-methyl-propanamide, methanesulfonate;
FCE 26742A* means (S)-2-(4-(2-fluorobenzyloxy) benzylamino) propanamide, methanesulfonate;
FCE 29644A means 2-(4-(3-chlorobenzyloxy) benzylamino)-2-methyl-propanamide, methanesulfonate;
FCE 26193A* means (S)-2-(4-(3-chlorobenzyloxy) benzylamino) propanamide, methanesulfonate;
FCE 29645A means 2-(4-(4-fluorobenzyloxy) benzylamino)-2-methyl-propanamide, methanesulfonate;
FCE 26998A* means (S)-2-(4-(4-fluorobenzyloxy) benzylamino) propanamide, methanesulfonate;
FCE 29647A means 2-(4-(3-fluorobenzyloxy) benzylamino)-2-methyl-N-methylpropanamide, methanesulfonate;
FCE 28657A* means (S)-2-(4-(3-fluorobenzyloxy) benzylamino)-N-methylpropanamide, methanesulfonate.

The comparative activity test data set out in the above table show that the new compounds of the instant invention are from 2 to 4 fold more active than the closely related prior art compounds.

A patient is treated according to the present invention by a method comprising administering to the patient an effective amount of one of the compounds of the invention. In this way the present compounds can be used to treat disorders of the central nervous system, for example epilepsy or Parkinson's disease; or as neuroprotective agents, anti-depressants, hypnotics or anti-spastic agents. The condition of a patient may thus be improved.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous injection or infusion.

The dosage depends on the age, weight, conditions of the patient and on the administration route; for example, the dosage adopted for oral administration to adult humans e.g. for the representative compound of the invention 2-[4-(3-fluorobenzyloxy)benzylamino]-2-methyl-propanamide may range from about 1 to about 500 mg pro dose, from 1 to 5 times daily.

The invention includes pharmaceutical compositions comprising a compound of the invention, as an active principle, in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, destrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersion for oral administration may be e.g. syrups, emulsions and suspension.

The syrups may contain as carrier, for example, saccharose or saccharose with glycerine and/or mannitol and/or sorbitol.

The suspension and the emulsion may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the invention.

EXAMPLE 1

2-[4-(3-fluorobenzyloxy) benzylamino]-2-methyl-propanamide, methanesulfonate (FCE 29088A)

To a solution of 2-amino-2-methylpropanamide, hydrochloride (7.01 g; 0.051 mol) in anhydrous methanol (160 ml), under stirring and nitrogen, 7.0 g of 3 Å molecular sieves were added and then, in a single portion, $NaBH_3CN$ (2.31 g; 0.037 mol), after 10 minutes, 10.6 g (0.046 mol) of 4-(3-fluorobenzyloxy) benzaldehyde were added, in 140 ml of anhydrous methanol. After 24 hours the reaction was completed, the mixture filtered, the solution was evaporated to give a residue which was directly flash-chromatographed on silica gel (eluant: $CHCl_3$ 98: $CH_3OH$ 2: 30% $NH_4OH$ 0.15) to afford a white solid (6.2 g; 43%). The free base thus obtained was treated with a stoichiometric amount of methanesulfonic acid to yield the title compound (m.p. 209–213° C.).

Analogously, the following products can be obtained, starting from the corresponding aldehyde and the appropriate amide:

2-[4-(3-chlorobenzyloxy) benzylamino]-2-methyl-propanamide, methanesulfonate, m.p 202–206° C. (FCE 29644A);

2-[4-(3-bromobenzyloxy)benzylamino]-2-methyl-propanamide, methanesulfonate, m.p. 197–202° C. (FCE 29494A);

2-[4-(4-fluorobenzyloxy)benzylamino]-2-methyl-propanamide, methanesulfonate, m.p. 233° C. (FCE 29645A);

2-[4-(2-fluorobenzyloxy)benzylamino]-2-methyl-propanamide, methanesulfonate, m.p. 215–220° C. (FCE 29484A);

2-[4-(3-fluorobenzylamino)benzylamino]-2-methyl-propanamide, dihydrochloride, m.p. 165° ca. (dec.) (FCE 29822A);

2-[(4-benzylsulfanyl)benzylamino]-2-methyl-propanamide, methanesulfonate, m.p. 214–215° C. (FCE 29482A)

2-[4-(3-fluorobenzyloxy)benzylamino]-2-methyl-N-methyl-propanamide, methanesulfonate, m.p. 213–218° C. (FCE 29647A); and 2-[4-(4-chlorobenzyloxy)benzylamino]-2-methyl-propanamide, m.p. 226–227° C. (FCE 29485A)

EXAMPLE 2

2-{[4-(3-fluorobenzyloxy)benzyl]methylamino}-2-methyl-propanamide (FCE 29486)

One g. (0.00316 mol) of 2-[(4-(3-fluorobenzyloxy)benzylamino]-2-methyl-propanamide are dissolved in acetonitrile (50 ml) under a nitrogen stream. To this mixture, 3.16 ml (0.0389 mol) of 37% formaldehyde and 0.29 g (0.00460 mol) of sodium cyanoborohydride are added at room temperature. After 20 minutes, glacial acetic acid is dropped up to neutrality of the solution. The mixture is stirred for 40 minutes and evaporated to dryness. 40 ml of 2N KOH are added to the residue. After extracting with ethyl acetate, washing with N/2 KOH and then with water and brine, the organic layer is dried on $Na_2SO_4$, then filtered and evaporated to obtain a residue which is flash-chromatographed on silica gel (eluant: $CHCl_3$ 200: $CH_3OH$ 3: 30% $NH_4OH$ 0.2) to give 0.75 (72%) of a white solid (m.p. 121–123° C.).

Analogously the following products can be prepared starting from the corresponding secondary amine:

2-{[4-(3-chlorobenzyloxy)benzyl]methylamino}-2-methyl-propanamide; and

2-{([4-(3-bromobenzyloxy)benzyl]methylamino}-2-methyl-propanamide.

EXAMPLE 3

With the usual methods of pharmaceutical technique, preparation can be made of capsules having the following composition:

| | |
|---|---|
| 2-[4-(3-fluorobenzyloxy)benzylamino]-2-methyl-propanamide, methanesulfonate | 50 mg |
| Talc | 2 mg |
| Corn starch | 2 mg |
| Microcristalline cellulose | 6 mg |
| Magnesium stearate | 1 mg |

We claim:

1. A compound of formula (I)

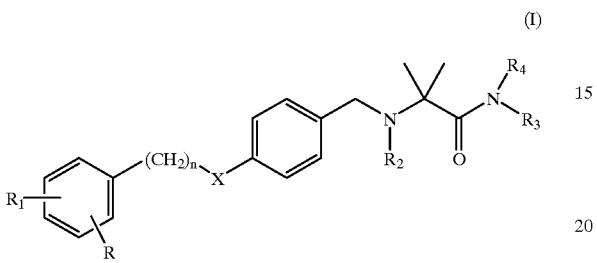

wherein:

n is zero, 1, 2 or 3;

X is —O—, —S—, —CH$_2$— or —NH—;

each of R and R$_1$ independently is hydrogen, C$_1$–C$_6$ alkyl, halogen, hydroxy, C$_1$–C$_4$ alkoxy or trifluoromethyl;

each of R$_2$, R$_3$ and R$_4$ independently is hydrogen, C$_1$–C$_6$ alkyl or C$_3$–C$_7$ cycloalkyl; or a pharmaceutically acceptable salt thereof with a proviso that when X is —S— and R, R$_1$, R$_2$, R$_3$, R$_4$ are hydrogen, n is not zero.

2. A compound of formula (I), according to claim 1, wherein:

n is 1 or 2;

X is —O—, —S— or —NH—; R is hydrogen; R$_1$ is hydrogen or halogen;

each of R$_2$, R$_3$, R$_4$ independently is hydrogen or C$_1$–C$_4$ alkyl; or a pharmaceutically acceptable salt thereof.

3. A compound of formula (I), according to claim 1, wherein:

n is 1;

X is —O—, —S— or —NH—;

R$_1$ is hydrogen or halogen;

R, R$_1$, R$_2$, R$_3$ and R$_4$ are hydrogen; or a pharmaceutically acceptable salt thereof.

4. A compound selected from the group consisting of:

2-[4-(3-fluorobenzyloxy)benzylamino]-2-methyl-propanamide;

2-[4-(3-chlorobenzyloxy)benzylamino]-2-methyl-propanamide;

2-[4-(4-chlorobenzyloxy)benzylamino]-2-methyl-propanamide;

2-[4-(3-bromobenzyloxy)benzylamino]-2-methyl-propanamide;

2-[4-(4-fluorobenzyloxy)benzylamino]-2-methyl-propanamide;

2-[4-(2-fluorobenzyloxy)benzylamino]-2-methyl-propanamide;

2-[4-(benzylsulfanyl)benzylamino]-2-methyl-propanamide;

2-{[4-(3-fluorobenzyloxy)benzyl]-methylamino}-2-methyl-propanamide;

2-[4-(3-fluorobenzyloxy)benzylamino]-2-methyl-N-methyl-propanamide;

2-{[4-(3-chlorobenzyloxy)benzyl]methylamino}-2-methyl-propanamide; and

2-{[4-(3-bromobenzyloxy)benzyl]methylamino}-2-methyl-propanamide, if the case, either as single (S) or (R) isomer or as a mixture thereof, or a pharmaceutically acceptable salt thereof.

5. A process for the preparation of a compound of formula (I), as defined in claim 1, or a pharmaceutically acceptable salt thereof, the process comprising:

a) reacting a compound of formula (II)

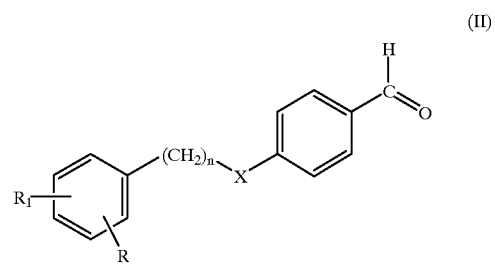

wherein n, R, R$_1$ and X are as defined in claim 1, with a compound of formula (III)

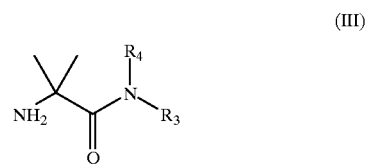

wherein R$_3$ and R$_4$ are as defined in claim 1, thus obtaining a compound of formula (I) in which R$_2$ is hydrogen; or b) reacting a compound of formula (IV)

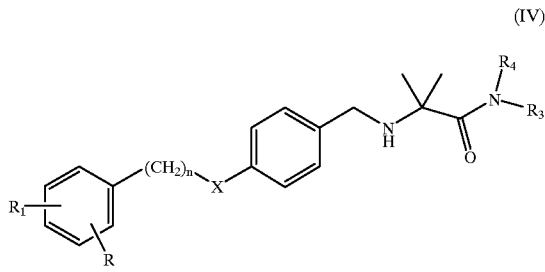

wherein R, R$_1$, R$_3$, R$_4$, n and X are as defined in claim 1, with a compound of formula (V) or (VI)

wherein W is a halogen atom; R'$_2$ is a C$_1$–C$_6$ alkyl and R''$_2$ is hydrogen or C$_1$–C$_5$ alkyl, thus obtaining a compound of the invention in which R$_2$ is C$_1$–C$_6$ alkyl; and, if desired, converting a compound of the invention into another compound of the invention and/or, if desired, converting a compound of the invention into a pharmaceutically acceptable salt and/or, if desired, converting a salt into a free compound.

6. A pharmaceutical composition containing a suitable carrier and/or diluent and, as an active principle, a compound of formula (I), as defined in claim 1, or a pharmaceutically acceptable salt thereof.

7. A method for treating a disorder of the central nervous system in a patient in need of the treatment, comprising administering an effective amount of the compound of claim 1, or a pharmaceutically acceptable salt thereof, to said patient.

8. A method for treating epilepsy, Parkinson's disease, or a neurodegenerative disease in a patient in need of the treatment, comprising administering an effective amount of the compound of claim 1, or a pharmaceutically acceptable salt thereof, to said patient.

9. The method of claim 8, wherein said neurodegenerative disease is amyotrophic lateral sclerosis, Down's syndrome, Huntington's disease, dementia caused by acquired immunodeficiency syndrome, infarctual dementia, an infection or inflammation of the brain.

10. A method for treating neuronal loss associated with stroke, hypoxia, ischemia, central nervous system trauma, hypoglycemia or surgery in a patient in need thereof, comprising administering an effective amount of the compound of claim 1, or a pharmaceutically acceptable salt thereof, to said patient.

11. A method for treating ocular damage or retinopathy in a patient in need of the treatment, comprising administering an effective amount of the compound of claim 1, or a pharmaceutically acceptable salt thereof, to said patient.

12. A method for treating a neurological disorder which is treatable by a hypnotic, antidepressant or antispastic agent in a patient in need of the treatment, comprising administering an effective amount of the compound of claim 1, or a pharmaceutically acceptable salt thereof, to said patient.

* * * * *

UNITED STATES PATENT AND TRADEMARK OFFICE
CERTIFICATE OF CORRECTION

PATENT NO. : 5,945,454

DATED : August 31, 1999

INVENTOR(S) : Paolo Pevarello, Raffaella Amici, Mario Varasi, Alberto Bonsignori, Patricia Salvati It is certified that errors appear in the above-identified patent and that said Letters Patent is hereby corrected as shown below:

Claim 1, the last line, after "n is not", delete "zero" and insert therefor --one--.

Claim 4, line 14, delete "2-[4-(benzylsulfanyl)benzylamino]-2-methyl-" and insert therefor -- 2-[4-(3-fluorobenzylamino)benzylamino]-2-methyl- --.

Signed and Sealed this

Twelfth Day of September, 2000

*Attest:*

Q. TODD DICKINSON

*Attesting Officer*      *Director of Patents and Trademarks*